United States Patent [19]

Goulas et al.

[11] 4,348,111
[45] Sep. 7, 1982

[54] OPTICAL PARTICLE ANALYZERS

[75] Inventors: Apostolos Goulas, Cranfield; Brian R. Moon, Narborough; Michael M. Ross, Lutterworth, all of England

[73] Assignee: The English Electric Company Limited, London, England

[21] Appl. No.: 98,852

[22] Filed: Nov. 30, 1979

[30] Foreign Application Priority Data

Dec. 7, 1978 [GB] United Kingdom ............... 47572/78

[51] Int. Cl.³ .......................................... G01N 15/02
[52] U.S. Cl. .................................. 356/336; 356/338; 356/342; 356/346
[58] Field of Search ................ 356/336, 338, 342, 343

[56] References Cited

U.S. PATENT DOCUMENTS

| | | |
|---|---|---|
| 3,563,660 | 2/1971 | Soloway et al. |
| 3,851,169 | 11/1974 | Faxvog |
| 3,873,204 | 3/1975 | Friedman et al. |
| 3,941,477 | 3/1976 | Schodl ..................... 356/343 X |
| 3,960,449 | 6/1976 | Carleton et al. |
| 3,992,103 | 11/1976 | Tyley et al. |
| 4,011,459 | 3/1977 | Knollenberg et al. |
| 4,125,778 | 11/1978 | Smart ..................... 356/342 X |
| 4,140,395 | 2/1979 | Kreikebaum ............. 356/336 |
| 4,146,799 | 3/1979 | Pitt et al. ............... 356/343 X |
| 4,152,070 | 5/1979 | Kushner et al. .......... 356/343 |

FOREIGN PATENT DOCUMENTS 2732272 10/1978 Fed. Rep. of Germany.

Primary Examiner—John K. Corbin
Assistant Examiner—Matthew W. Koren
Attorney, Agent, or Firm—Kirschstein, Kirschstein, Ottinger & Cobrin

[57] ABSTRACT

An optical particle analyzer in which the size of a particle in a particle stream is determined from the intensity or the duration of light scattered from it. A laser beam is directed transversely onto the stream and scattering occurs at the beam focus. To ensure that only particles which traverse the center of the beam are considered, a smaller, validating beam concentric with the main beam also produces scattered light. A pulse from the narrow beam coincident with one from the broad beam confirms that the associated particle has passed through the center of the broad beam and warrants consideration and assessment.

A further narrow beam spaced from the first provides a time delay, dependent on particle velocity, between interception of the two narrow beams by a particle. Particle velocity is thus measured.

6 Claims, 5 Drawing Figures

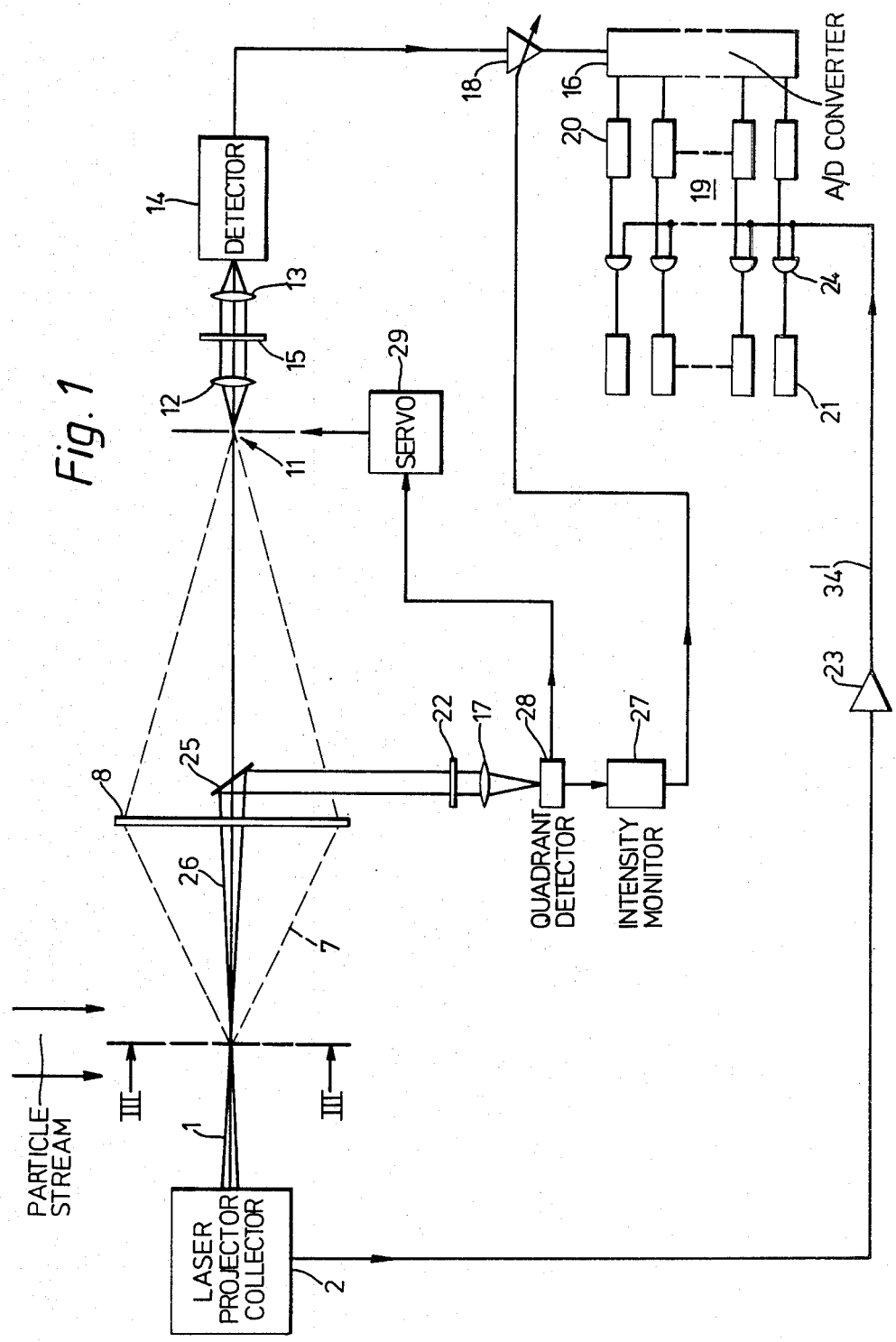

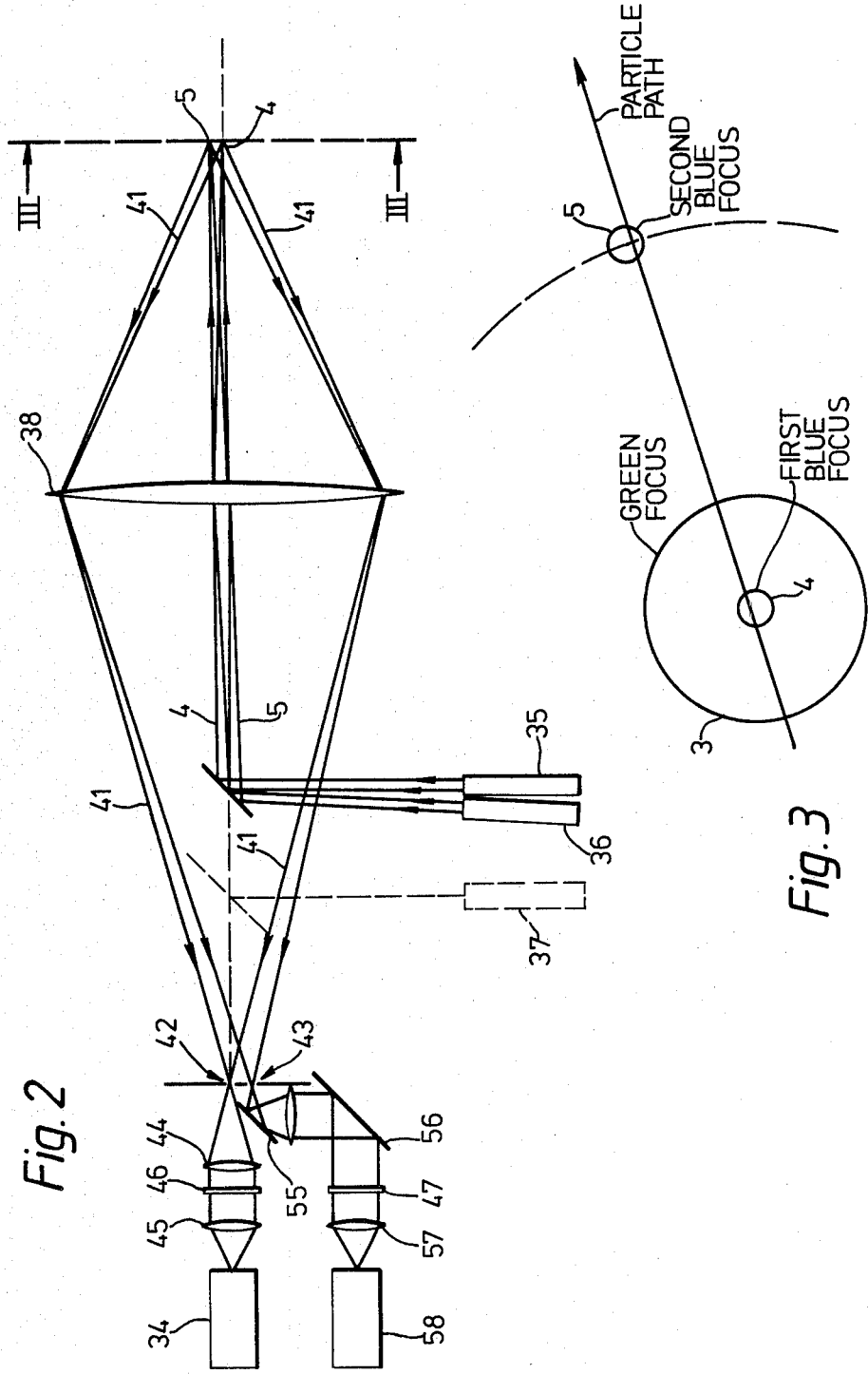

OPTICAL PARTICLE ANALYZERS

This invention relates to an optical particle analyser and is particularly concerned with the size, and optionally the velocity, of particles in a stream of particles. One application of such equipment is to the sizing of ash particles in the gas flow from a fluidised bed combustor of a gas turbine engine. The invention is not limited to such an application however.

It is known that when a particle passes through a light beam, light is scattered by the particle, the amount of scattered light depending upon the size of the particle among other factors. However, where the path of a particle is uncertain, as in a stream of particles, it is difficult to determine how much, and which part, of the light beam is incident upon each particle. Where laser beams are used, this difficulty is particularly troublesome, since the intensity of the beam varies according to a Gaussian distribution throughout the cross section.

It is an object of the present invention to provide an optical particle analyser in which this difficulty is overcome.

Thus, according to the present invention, an optical particle analyser, wherein in operation a stream of particles is subjected to incident light, includes means for recording a pulse of light scattered from one of said particles as the particle traverses a first predetermined volume in the stream, means for recording a pulse of light scattered from one of the particles as the particle traverses a second predetermined volume much smaller than the first volume and lying in a fixed position within it, validation means for selecting only those light pulses in respect of the first volume which are in coincidence with light pulses in respect of the second volume, and assessment means for assessing a particle-size dependent factor of the selected light pulses.

The first and second volumes may be defined by incident light beams of different cross section and different frequencies, frequency selective means being provided to distinguish light scattered from the two beams.

Light scattered from the two beams is preferably focussed at respective apertures which further define the said first and second volumes.

The light beam may be concentric laser beams having a common focal plane intersecting the first and second volumes.

The assessment means may include optical detector means positioned forward of the first and second volumes in relation to the direction of the incident light, to detect forward scattered light from the first volume, and optical detector means positioned rearward of the first and second volumes to detect back scattered light from the second volume. Alternatively, the assessment means may include optical detector means positioned forward of said first and second volumes in relation to the direction of the incident light, to detect light scattered from both the first and second volumes in a forward direction.

In a further alternative arrangement, the first and second volumes may be defined by a single beam of light of cross section corresponding to the first volume, in combination with optical means of physical size corresponding to the second volume for separating light scattered from the second volume from light scattered from the remainder of the first volume.

Means may be provided for deriving a reference light level from light unscattered by particles, the magnitude of a pulse of scattered light being modified by the reference light level to take account of variations in incident light level.

The assessment means may be responsive to the intensity or to the duration of each selected light pulse.

There is preferably included analogue/digital converting means providing a digital representation of the intensity or duration of each selected light pulse, a respective store for each value of the digital representation, and gate means enabled by a validating light pulse from the second volume to load the digital representation into its associated store. The store for each value of the digital representation may comprise a counter providing a count of the number of pulses of a given intensity, the counters providing in combination a histogram of the distribution of particle size.

According to a feature of the invention, the analyser may include a third predetermined volume equal to the second predetermined volume but displaced from it by a predetermined distance along a path parallel to the stream of particles, the third volume being defined by the focus of a third laser beam in the focal plane, the analyser further including means providing representations of time interval between light pulses arising from the second and third volumes thereby providing an indication of particle velocity in the stream. The third laser beam may be rotatable about the second laser beam so that a line between their foci can be arranged at any angle to the particle stream, the analyser including analogue/digital converting means providing a digital representation of the time interval between a particle intercepting the second and third laser beams, and a counter in respect of each value of the digital representation, the counter providing a count of the number of occurrences of the particular time interval, and the counters providing in combination a histogram of the distribution of time interval values, alignment of the above line between foci with the particle stream direction being indicated by the degree of predominance of a particular time interval value.

Where light scattered from that first volume is focussed at an aperture which further defines the first volume, means may be provided for locating the axis of the light incident upon the second volume and controlling the transverse position of the aperture to align it with the focus of the scattered light. The means for locating the axis of the light incident upon the second volume may be selectively responsive to the frequency of the associated beam.

One embodiment of an optical particle analyser in accordance with the invention, and modifications thereof, will now be described, by way of example, with reference to the accompanying drawings, of which:

FIG. 1 is a diagrammatic illustration of one embodiment of a laser particle analyser according to the invention;

FIG. 2 is a diagrammatic illustration of a detail of FIG. 1;

FIG. 3 is a diagram, on a much enlarged scale, of light beam cross sections in the plane III—III of FIG. 1;

Figure 4:
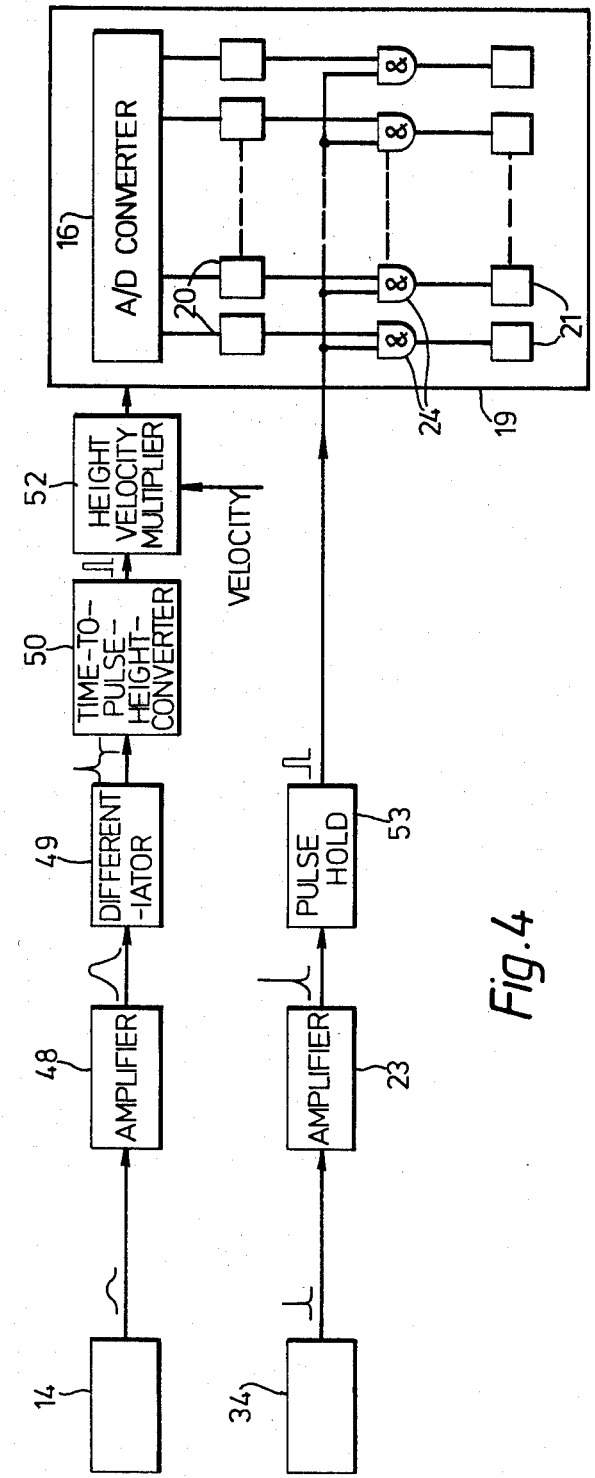
FIG. 4 is a block diagram of a modification of the embodiment of FIG. 1 in which particle size is derived from light pulse duration.

Referring to FIG. 1, a stream of particles in a duct, not shown, is intercepted by three laser beams referenced jointly 1 and shown as coincident, which focus in a common focal plane III—III lying parallel to the path of the particle stream and approximately mid way through the stream. The duct is provided with windows (not shown) for the transmission of the laser beams.

The laser beams are provided by a projector arrangement 2 incorporating an argon ion laser which operates at two wavelengths, producing one green beam of wavelength 514.5 nm, and two blue beams each of 488 nm wavelength. The disposition of these beams is shown in FIG. 3, which is a section in the focal plane III—III. The green beam 3 is focussed to a relatively large cross section while one blue beam 4 is coaxial with the green beam and is focussed to a very much smaller cross section. The second blue beam 5 is displaced from the first one by a small distance of about 0.5 mm in the focal plane and can be rotated around the beam 4 so that a line between their foci can be arranged at any angle to the particle stream.

The sizes of the different beams in the focal planes is determined by the anticipated particle size. The green beam cross section is required to be several times larger than the particles while the blue beams are required to be of comparable size with the particle or smaller. In a combustor output duct feeding a gas turbine the maximum ash particle size may be up to 30 microns. A suitable size for the focussed green beam is then 100 microns and for the blue beams 10 microns.

The laser beams are scattered on impact with particles at the focal plane. The basic region in which scattering of the green beam occurs is thus the volume defined by the cross section of the beam 3 in the particle stream and of small extent on each side of the focal plane. Similar volumes are effective for the two blue beams 4 and 5. These volumes are, however, further defined by apertures on which the scattered light is focussed, as will be explained.

Sizing of the particles is achieved by the coaxial beams 3 and 4 and FIG. 1 illustrates this aspect only. The scattered light 7, from the interception of the green and blue beams by a particle, is collected by a lens 8 and focussed on to a pinhole 11 which is of a size such as to further define the 'green volume' of interception. Light emerging from the pinhole 11 is collimated by a lens 12 and re-focussed by a lens 13 on to an optical detector 14. The light passed by the pinhole 11 does, of course, include green and blue light whereas the quantitative assessment of the scattered light is to be based on the green light only. This is because only the green beam 3 has sufficient cross section to permit a particle, of the size in question, to lie substantially entirely within the peak level of the Gaussian distribution in which situation the size can be related to the amount of scattered light. A frequency responsive filter 15 is therefore placed in the collimated beam so as to pass only the green light. A pulse of green light is therefore detected by the detector 14, the detector producing a corresponding signal pulse.

The pulse from the detector 14 will have both an amplitude and a duration which are dependent upon the particle size. In FIG. 1, the amplitude factor is used for the size assessment. The detector 14 output pulse is amplified by a gain-controlled amplifier 18 and applied to a multichannel analyser circuit 19. This circuit incorporates an analogue/digital converter 16 which encodes the height of the pulse binarily, and distributes a "1" to the appropriate one of a series of buffer stores 20 according to the magnitude of the binary number. Thus a '1' is stored in an appropriate buffer store 20 for each pulse of scattered green light detected by the detector 14. Each buffer store 20 can only hold an indication of one green light pulse so it is connected to its own counter 21 for storing or counting the light pulses of the particular amplitude.

The object of the particular arrangement is to accept only those 'green' pulses which arise from particles traversing the peak intensity portion of the beam in the cross section 3, i.e. particles which traverse the centre of the 'green volume'. A validation signal is therefore required to select only those 'green' pulses.

The derivation of this validation signal is illustrated in FIG. 2 which shows the salient features of the laser projector of FIG. 1, with particular reference to the detection of scattered blue light.

The blue light sources are shown as separate sources 35, 36 and the green light source 37 in broken lines, for simplicity. The arrangement of the beam sources produces coaxial beams 3 and 4 and a slightly off-axis beam 5 as previously explained, the beams being focussed in the plane III—III by the projector lens 38. While the green scattering light that is detected is forward scattered light, the validation signal is derived from back scattered blue light.

Both blue beams 4 and 5 are illustrated in FIG. 2 but it is only the axial beam 4 which is used for the validation signal. The off-axis beam 5 is employed for velocity measurement as will be explained. Scattered blue light, from the beam 4 is focussed by the projector lens 38 on to the axial one of two adjacent pin holes 42 and 43 thus further defining the 'blue volume' of interception of the blue beam 4 by particles in the stream. The blue light so focussed is collimated by lenses 44 and 45 and refocussed onto an optical detector 34. The resulting output pulse from this detector provides the necessary validation signal, after amplification and shaping, for the logic circuitry 19 of FIG. 1. The validation signal appears on lead 34' in FIG. 1.

It will be clear that, because of the small size of the blue beam 4, if an intercepting particle is off-centre in the green beam 3 it will not intercept the blue beam 4, no blue light will be scattered and no validation signal will arise from the blue pulse detector 34. A validation pulse, when it arises, is amplified by amplifier 23 and applied to AND-gates 24 in the logic circuitry 19. An indication of a 'green' pulse which arises at the same time as a 'blue' pulse, and which will be stored in one or other of the stores 20, will therefore be passed by an AND-gate 24 to the associated counter 21 which accumulates a count of all particles of that particular size. The counters 21 thus provide a histogram of the incidence of various particle sizes. The particle density of the stream can also be obtained by timing the accumulation of pulse counts in the counters 21. The counters 21 can either be enabled for a predetermined time interval or separate counters running in parallel with the counters 21 can be similarly enabled for a predetermined time. If a total particle count is required a summing circuit can be loaded with the separate counts after a predetermined interval.

The level of the scattered light is, of course, dependent upon the level of the incident light. In order to monitor this factor continuously, a mirror 25 is positioned to divert the unscattered light 26 to a level monitor 27 which supplies a gain-control signal to the amplifier 18 to control the gain inversely with the level of the incident light. The green pulse signal level is therefore stabilised against beam intensity variations.

Instead of supplying the diverted beam 26 directly to the level monitor 27, it is first focussed by a lens system 17 and a blue-pass filter 22, and the lateral position of the focus, off-axis, determined by a 4-quadrant detector 28 in known manner. The coordinates of the focus, which ideally should be on the diverted optical axis, are then used as inputs to a servo system 29 which in turn controls the position of the pinhole 11 in 'x' and 'y' directions. The pinhole 11 is thus positioned centrally on the re-focussed scattered light even if this position is not accurately on the optical axis of the system.

FIG. 4 illustrates a modification employing an alternative form of the detection circuitry of FIG. 1, and in which the size of a particle is assessed by virtue of the duration, rather than the intensity of a pulse of scattered light. The assessment pulse of green light is again provided by the optical detectors 14, and a validating pulse by the 'blue' optical detector 34. The assessment pulse is applied to an amplifier 48 and then a differentiator 49 which produces, in known manner, two sharp pulses at the rise and fall of theoutput pulse of the amplifier 48. Circuitry 50 converts the time interval between these pulses to a pulse height, which is then applied to the logic circuitry 19 by way of an analogue velocity/time multiplier 52. Alternatively, the particle velocity can be digitally encoded and digitally multiplied by the pulse duration after analogue/digital conversion in the logic circuitry 19. The validating pulse from optical detector 34 is again amplified and extended by a 'pulse hold' circuit 53 to cover the period of the storage of the assessment pulse in store 20.

Figure 5:
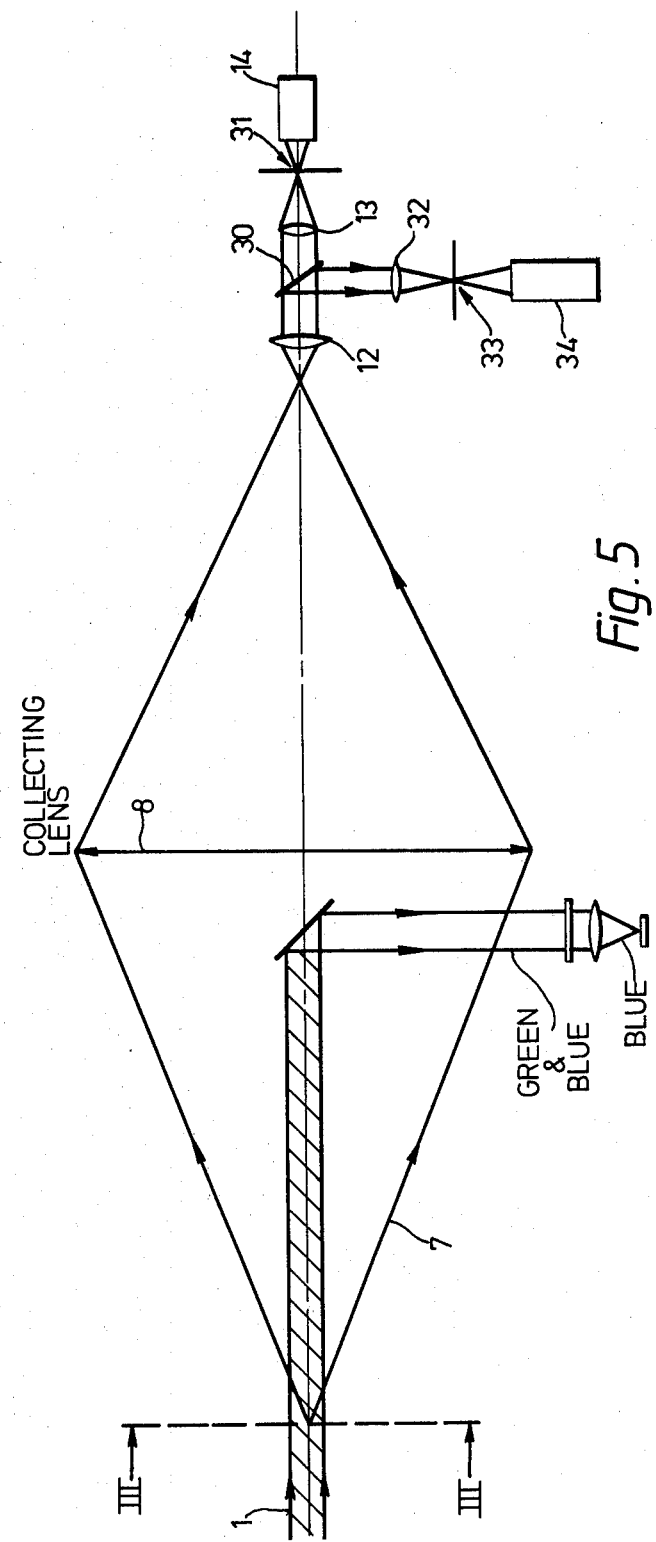
FIG. 5 illustrates a further modification of the embodiment of FIG. 1 employing a different method of deriving a validation signal.

A further modification of the arrangement of FIG. 1 is shown in FIG. 5. In this case both assessment and validating pulses are obtained from forward scattered light which diverges from the plane III—III and is collected by the lens 8. Both green and blue light are then focussed and collimated by lens 12. Interposed in the collimated beams is a dichroic mirror 30 which is frequency selective so that it transmits green light and reflects blue light. The green light is thus focussed on a pin hole 31 by way of a lens 13 and the blue light is similarly focussed on a pinhole 33 by way of a lens 32. The pin holes 31 and 32 have relative sizes corresponding to the green and blue volumes as before.

Assessment and validation pulses are then obtained from the optical detectors 14 and 34 as before.

A further modification illustrated in FIG. 5 is the absence of focussing of the laser beams on the 'focal' plane III—III. In this case, while the green and blue beams in the vicinity of the 'focal' plane must still have their same relative cross sections, the definition of the green and blue volumes is determined by the apertures 31 and 32.

As mentioned previously, a further feature of the present particle analyser is the facility for particle velocity assessment which is known per se. Referring again to FIGS. 1, 2 and 3, the second blue beam 5 is focussed in the plane III—III at about 0.5 millimeters laterally displaced from the main blue focus 4. A particle which intercepts both blue beams will therefore produce successive back scattered light pulses separated by a time interval inversely proportional to the particle velocity. Light scattered from the blue beam 4 is detected by detector 34 as previously explained. Light scattered from blue beam 5 is focussed by the lens 38 on a pin hole 43 adjacent the aperture 42. Mirrors 55 and 56 divert the beam to provide spatial separation and room for installation of this optical path. A frequency selective filter 47, like the filter 46 in the validation beam path, passes blue light to its respective detector 58 and blocks any green light.

Pulses from the two detectors 34 and 58 are then amplified and the time interval between them is converted to a binary '1-out-of-n' code as in FIG. 4, by a time-to-pulse-height converter and A/D converter or by any other convenient means. No validating pulse is required in this case and the outputs of the stores 20 are connected to the counters 21 without the intervening AND-gates.

It will be clear that if the orientation of the two blue foci is such that the line between them is not aligned with the general particle movement then the time intervals between pulses from the two detectors will be meaningless since they will have arisen from different particles. The resulting histogram exhibited by the counters 21 would be substantially flat with no peak corresponding to any particular velocity (time interval).

To accommodate this possibility the off-axis blue beam 5 is rotatable about the beam 4 as illustrated in FIG. 3.

As the beam 5 is rotated about the axis of the beam 4 it will at some point lie on a line through the beam 4 which is parallel to the particle stream. In this case many particles will intercept both beams and a particular value of time delay will be dominant, corresponding to the most common particle velocity. The non-uniform spread of time-delays will then be a true indication of the velocity spread in the particle stream. The dominant velocity can be employed as the velocity input in FIG. 4.

It will be clear that although the radiation employed in the described embodiment has been referred to as "light", this implies no particular frequency restriction, for example to visible light, and the claims should be interpreted accordingly.

We claim:

1. An optical particle analyzer, wherein a stream of particles is subjected, in operation, to incident light, the arrangement including a first predetermined volume in said stream defined by a beam of light of a first frequency, a second predetermined volume in said stream defined by a beam of light of a second frequency, said second predetermined volume being smaller than said first volume and lying in a fixed position within it, means for recording a pulse of scattered light of said first frequency as one of said particles traverses said first predetermined volume, means for recording a pulse of scattered light of said second frequency as one of said particles traverses said second predetermined volume, validation means for selecting only those light pulses in respect of the first volume which are in coincidence with light pulses in respect of the second volume, and assessment means for assessing a particle-size dependent factor of the selected light pulses.

2. An analyzer according to claim 1, wherein light scattered from the two beams is focused at respective apertures which further define the said first and second volumes.

3. A particle analyzer according to claim 1, wherein said light beams are concentric laser beams having a common focal plane intersecting said first and second volumes and including a third predetermined volume equal to the second predetermined volume but displaced from it by a predetermined distance along a path parallel to said stream of particles, said third volume being defined by the focus of a third laser beam in said focal plane, the analyzer further including means providing representations of time intervals between light pulses arising from said second and third volumes thereby providing an indication of particle velocity in the stream.

4. An analyzer according to claim 3, wherein said third laser beam is rotatable about the second laser beam so that a line between their foci can be arranged at any angle to the particle stream, the analyzer including analogue/digital converting means providing a digital representation of the time between a particle intercepting the second and third laser beams, and a counter in respect of each value of said digital representation, the counter providing a count of the number of occurrences of the particular time interval and the counters providing in combination a histogram of the distribution of time interval values, alignment of said line between foci with the particle stream direction being indicated by the degree of predominance of a particular time interval value.

5. An analyzer according to claim 1, wherein said assessment means includes optical detector means positioned forward of said first and second volumes in relation to the direction of the incident light, to detect forward scattered light from said first volume, and optical detector means positioned rearward of said first and second volumes to detect back scattered light from said second volume, and wherein light scattered from said first volume is focused at an aperture which further defines the first volume, means being provided for locating the axis of the light incident upon said second volume and controlling the transverse position of said aperture to align it with the focus of the scattered light.

6. An analyzer according to claim 1, including an aperture upon which light scattered from said first volume is focused to further define the first volume, and means for locating the axis of the light incident upon said second volume and controlling the transverse position of said aperture to align it with the focus of the scattered light, said means for locating the axis of the light incident upon said second volume being selectively responsive to the frequency of the associated beam.

* * * * *